US00PP18883P3

(12) United States Plant Patent
Layt

(10) Patent No.: US PP18,883 P3
(45) Date of Patent: Jun. 3, 2008

(54) ***DIANELLA REVOLUTA* PLANT NAMED 'DTN03'**

(50) Latin Name: *Dianella revoluta*
Varietal Denomination: DTN03

(75) Inventor: Todd Anthony Layt, New South Wales (AU)

(73) Assignee: VersaScapes L.L.C., Mt. Pleasant, SC (US)

( * ) Notice: Subject to any disclaimer, the term of this patent is extended or adjusted under 35 U.S.C. 154(b) by 56 days.

(21) Appl. No.: 11/351,912

(22) Filed: Feb. 10, 2006

(65) Prior Publication Data

US 2006/0185048 P1 Aug. 17, 2006

Related U.S. Application Data

(60) Provisional application No. 60/652,203, filed on Feb. 11, 2005.

(51) Int. Cl.
*A01H 5/00* (2006.01)

(52) U.S. Cl. ..... Plt./263; Plt./384

(58) Field of Classification Search ..... Plt./263, Plt./384

See application file for complete search history.

(56) References Cited

PUBLICATIONS

Layt; "*Dianella revoluta* flax lily 'DTN03'," *Plant Varieties Journal* 17 (1):27–28,133,145–6,585–87 (Apr. 28, 2004).*

* cited by examiner

*Primary Examiner*—Kent Bell
*Assistant Examiner*—Louanne Krawczewicz Myers
(74) *Attorney, Agent, or Firm*—Myers Bigel Sibley & Sajovec, P.A.

(57) ABSTRACT

'DTN03' is a distinctive variety of *Dianella revoluta,* which is characterized by its combination of bluish-green leaf color, strong leaf glaucosity, very short height, erect growth habit, very dense shoots with very short internodes, and narrow leaf blade. Pale blue flowers on stems up to 50 cm high typically develop in spring and early summer and are followed by green berries.

2 Drawing Sheets

Latin name of the genus and species: The Latin name of the novel variety disclosed herein is *Dianella revoluta* 'DTN03'.

Variety denomination: The inventive variety of *Dianella revoluta* disclosed herein has been given the variety denomination 'DTN03'.

BACKGROUND OF THE INVENTION

The present invention relates to a new and distinct variety of evergreen perennial *Dianella revoluta,* which has been named 'DTN03'. It is anticipated that the plant of this invention will be marketed under the tradename Baby Bliss. *Dianella* are a genus of ornamental grass-like plants in the Phormiaceae family. In general, *Dianella revoluta* has flax-like leaves with curved edges. Pale blue flowers on stems up to 50 cm high typically develop in spring and early summer and are followed by green berries.

Lineage: The cultivar 'DTN03' was discovered in 1996 in Clarendon, New South Wales, Australia, during a seedling selection of cultivated *Dianella revoluta* 'DR4000' (unpatented). The parent 'DR4000' is characterized by a wide leaf with medium glaucosity, tall plant height, and medium plant density. Selection criteria for 'DTN03' were bluish-green leaf color, strong leaf glaucosity, and short plant height with a dense compact habit.

Asexual reproduction: The new variety 'DTN03' was first asexually propagated by vegetative division in the state of New South Wales, Australia in September 1998 and has been asexually propagated since that time by division and micropropagation. The distinctive characteristics of 'DTN03' have remained stable and true to type through successive cycles of asexual propagation.

SUMMARY OF THE INVENTION

'DTN03' is a distinctive variety of *Dianella revoluta,* which is characterized by its combination of bluish-green leaf color, strong leaf glaucosity, very short height, erect growth habit, very dense shoots with very short internodes, and narrow leaf blade. Pale blue flowers on stems up to 50 cm high typically develop in spring and early summer and are followed by green berries.

DETAILED BOTANICAL DESCRIPTION OF THE VARIETY

The following is a detailed botanical description of a new and distinct variety of *Dianella revoluta* known as 'DTN03' based upon observations of 15-month-old plants grown in 140 mm nursery pots in full sun in open beds in Clarendon, New South Wales, Australia. Color notations are based on The Royal Horticultural Society Colour Chart, The Royal Horticultural Society, London, 1995 edition.

Those skilled in the art will appreciate that certain characteristics will vary with older or, conversely, with younger plants. 'DTN03' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions.

'DTN03' is an evergreen perennial *Dianella revoluta.* 'DTN03' is a compact, erect plant with short internodes and an absence of aerial stems, very short plant height and narrow leaf blades with a bluish-green leaf color and strong leaf glaucosity. These characteristics are unusual for *Dianella revoluta,* as these plants are usually not very short and not as blue in color as 'DTN03'. A botanical description of 'DTN03' and comparisons with other varieties of *Dianella revoluta* are provided below.

Technical Description of the Variety

Plant characteristics: Growth habit erect, height very short (mean 16.4 cm), diameter 18–22 cm, very dense shoots with very short internodes and an absence of aerial stems, typical and observed number of plant shoots per cluster 10–15 with 5–7 leaves per shoot extended in a 6 month old plant.

Leaves: Attitude erect, arrangement dichotomous, length medium (12–16 mm), width narrow (mean 10.5 mm), upper side color yellow-green (RHS 147A), lower side color yellow-green (RHS 147A), glaucosity strong, resulting in blue-green overall appearance, texture of upper side and lower side smooth, shape ligulate, apex acute, base of blade sheathed, sheathes conduplicate, cross section concave, margin flat with spines present with weak prominence.

Basal sheath: Reddish coloration that occurs in some other *Dianella* is absent in 'DTN03'.

Basal shoots: Attitude erect, arrangement cluster.

Figure 2:
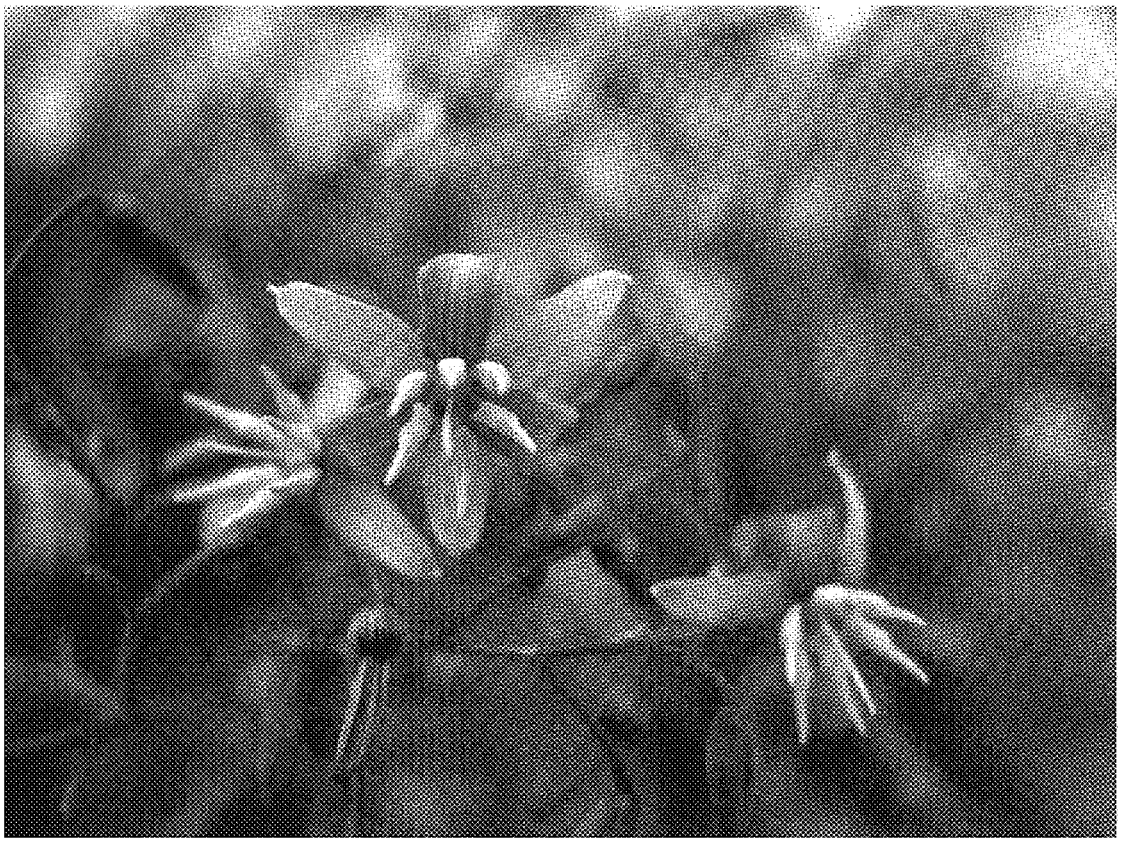
FIG. 2 shows the typical flowers of a *Dianella revoluta* 'DTN03' plant.

Flowers and berries: 'DTN03' has been observed for approximately four years and has produced pale blue flowers on stems up to 50 cm high. Flower type single. There may be 40 to 60 flowers per inflorescence on a mature shoot (lateral stem is not adequate for this species). Fragrance is absent. Peduncle diameter is 3–4 mm with medium strength and an upright attitude typical of the species. Peduncle color is yellow green (approximately RHS 146B–C). The flower buds are 8–10 mm long and 3–4 mm wide. Bud color changes from yellow green (RHS 147B) to violet blue (approximately RHS 89A) prior to opening. Mature flowers have 6 petals with ovate shape. Petal color (both upper and lower surfaces) is violet-blue (approximately RHS 94B–C). The three outer petals may have translucent tissue along midrib section. Petal apex is acute with a fused section at the midrib which may form a tuft. Petal attachment is sessile with an obtuse to truncate base. Petal margin is entire. Petal length is 8–9 mm and petal width is 3–4 mm. Flowers develop in spring and early summer and are followed by berries. Each inflorescence typically yields approximately 6–8 berries. Berry diameter is 8–10 mm and berry shape is globose. Unripe berry color is yellow green approx (RHS 146B) and ripe berry color is violet blue (RHS 89A). Flowers are shown in FIG. 2.

Reproductive organs: Mature flowers of 'DTN03' have 6 petals with ovate shape. Petal color is violet-blue (approximately RHS 94B). Anther number is 6 and filament color is yellow orange (approximately RHS 14A). Style is filiform and simple. Ovary color is yellow green RHS 146B–C. Flower diameter range is 9–13 mm. Petal attitude is strongly reflexed. Reproductive organs are typical of the species.

Cultural conditions: 'DTN03' can tolerate low nutrient conditions; it does not like continually wet soil conditions, but can tolerate well-draining sandy soils to very heavy clay soils. 'DTN03' is fairly adaptable to a wide range of soil pH.

Cold and heat tolerance: 'DTN03' has been observed to be cold tolerant to −12° C. in Clarendon, New South Wales, Australia. Foliage color did not change under these conditions, except for a slight burning at the very tips of the leaves. The plant has also been grown for two years in Charleston, S.C., USA and has remained evergreen down to −6° C.

'DTN03' is also very heat tolerant. It adapted well to the high heat conditions during summer in Clarendon, New South Wales, Australia and high heat and humidity conditions during summer in Charleston, S.C., USA without any noticeable disease or insect damage.

Drought tolerance: 'DTN03' has very good drought tolerance. 'DTN03' survived three months without rainfall under hot conditions in non-irrigated garden beds in summer in Clarendon. 'DTN03' has also been grown in non-irrigated beds in Charleston, S.C., USA for two years, and has been observed to go as long as 45 days without rainfall.

Pest resistance: No known pests. May be susceptible to root rot if in prolonged waterlogged soil conditions.

Figure 1:
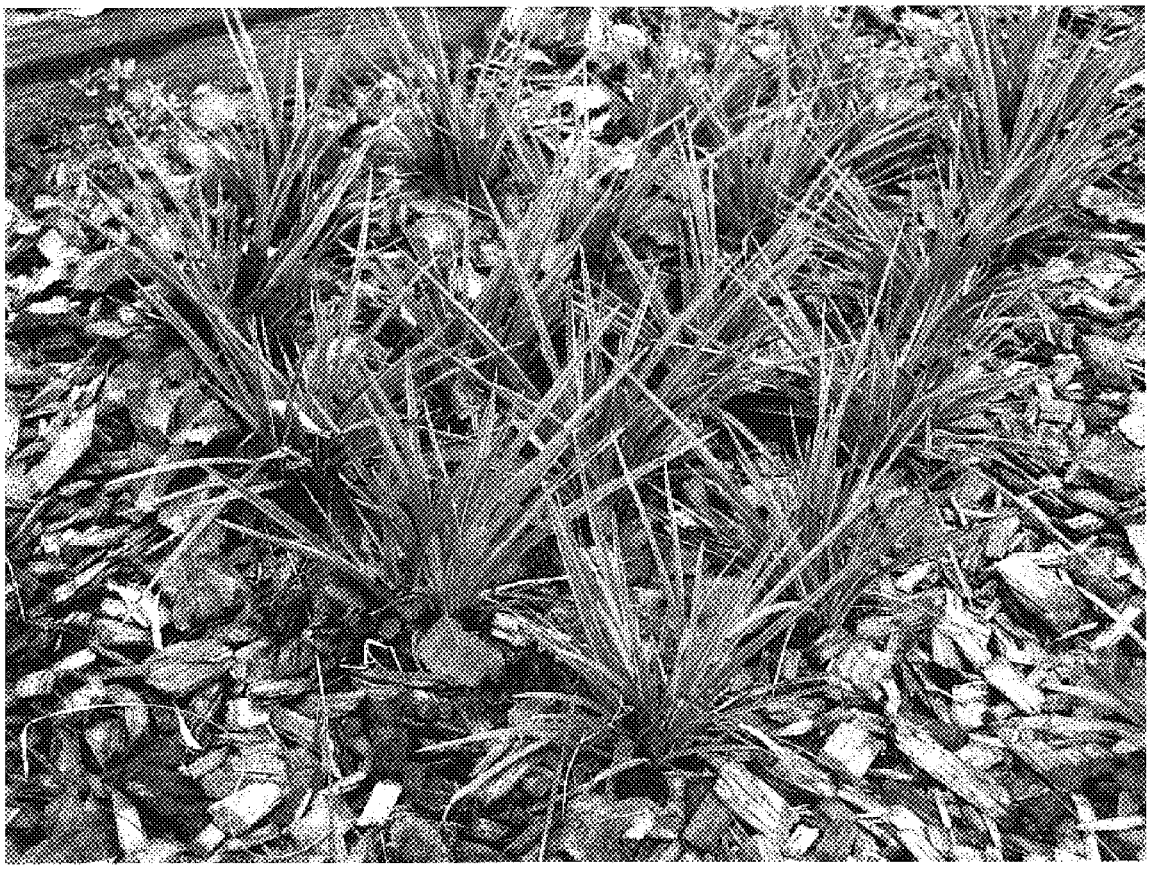
FIG. 1 shows an exemplary *Dianella revoluta* 'DTN03' plant at approximately 15 months of age. The plant was propagated in a greenhouse and was transferred to the field at six months and grown out in full sun for the final nine months.

These and other features and characteristics of 'DTN03' are apparent from FIG. 1.

Comparisons with Other *Dianella*

'DTN03' is a more attractive ornamental grass-like plant as compared with the parent 'DR4000'. 'DTN03' is characterized by a bluish-green leaf color, stronger leaf glaucosity, shorter plant height, and more compact plant habit with denser shoots as compared with 'DR4000'. The appearance of 'DTN03' is bluish, whereas 'DR4000' is more yellow-green in color (see Table 1).

*Dianella* 'DR5000' (U.S. Plant Pat. No. 17,719) is the most similar comparator variety to 'DTN03'. In comparison with 'DR5000', cultivar 'DTN03' has a shorter plant height with shorter internodes and an absence of basal sheath anthocyanin coloration. (see Table 1).

A comparative trial of *Dianella* cultivar 'DTN03' with 'DR4000' and 'DR5000' was carried out in summer 2003 to autumn 2004 in Clarendon, New South Wales, Australia. Plant observations and descriptions were taken in autumn 2004. The data are presented in Table 1 below. The plants for this trial were propagated from divisions, planted into 130 mm pots filled with soilless potting mix, and moved into 140 mm pots in full sun for nine months before the trial started. Nutrition was maintained with slow release fertilizers; pest and disease treatments were applied as needed. The trial was designed such that twenty plants of each variety were arranged in a completely randomized manner. Measurements were taken from ten plants at random with one sample per plant.

TABLE 1

| Characteristic | *Dianella* Variety | | |
|---|---|---|---|
| | 'DTN03' | 'DR5000' | 'DR4000' |
| Plant Height (cm) | | | |
| Mean | | 24.7 | 57.1 |
| Std Deviation | 16.4 | 1.9 | 4.9 |
| LSD/Sig. | 1.0 | P ≦ 0.01 | P ≦ 0.01 |
| | 4.33 | | |
| Density of Shoots | Strong | Strong | Weak |
| Leaf Width (mm) | | | |
| Mean | 10.5 | 9.1 | 10.4 |
| Std Deviation | 0.9 | 1.0 | 1.0 |
| LSD/Sig. | 1.8 | ns* | ns* |
| Leaf Glaucosity | Strong | Strong | Medium |
| Leaf Color | | | |
| Upper Side | 147A | 147A | 146A |

TABLE 1-continued

| Characteristic | *Dianella* Variety | | |
|---|---|---|---|
| | 'DTN03' | 'DR5000' | 'DR4000' |
| Lower Side | 147A | 189A | 146C-D |
| Overall appearance | Blue green | Blue green | Yellow green |
| Leaf cross section | Concave | Concave | Flat-revolute |
| Basal Sheath Color | Blue-green | Reddish-Brown | Red-Purple |
| Berry color | Green | Purple | Purple |

*ns—not significant

That which is claimed is:

1. A new and distinct variety of *Dianella revoluta* plant named 'DTN03', substantially as described and illustrated herein.

* * * * *